United States Patent
Porter

(10) Patent No.: US 9,358,208 B2
(45) Date of Patent: Jun. 7, 2016

(54) RECESSED BOLUS

(71) Applicant: ANIMAX LTD, Bury St. Edmunds, Suffolk (GB)

(72) Inventor: William Leslie Porter, Bury St Edmunds (GB)

(73) Assignee: Animax Ltd (GB)

( * ) Notice: Subject to any disclaimer, the term of this patent is extended or adjusted under 35 U.S.C. 154(b) by 175 days.

(21) Appl. No.: 13/914,251

(22) Filed: Jun. 10, 2013

(65) Prior Publication Data

US 2014/0228747 A1 Aug. 14, 2014

(30) Foreign Application Priority Data

Feb. 13, 2013 (GB) .................................. 1302507.7

(51) Int. Cl.

| A61K 9/00 | (2006.01) |
|---|---|
| A61K 47/44 | (2006.01) |
| A61K 9/22 | (2006.01) |
| A23K 1/16 | (2006.01) |
| A23K 1/18 | (2006.01) |
| A23P 1/08 | (2006.01) |
| A61K 33/18 | (2006.01) |
| A61K 9/02 | (2006.01) |

(52) U.S. Cl.
CPC ............... *A61K 9/0068* (2013.01); *A61K 9/025* (2013.01); *A61K 47/44* (2013.01)

(58) Field of Classification Search
CPC ...... A61K 9/0068; A61K 9/025; A61K 47/44
See application file for complete search history.

(56) References Cited

U.S. PATENT DOCUMENTS

| 3,336,200 | A | * | 8/1967 | Krause ..................... A23G 3/50 |
|---|---|---|---|---|
| | | | | 424/465 |
| 4,154,239 | A | * | 5/1979 | Turley .............................. 604/61 |
| 4,327,725 | A | | 5/1982 | Cortese |
| 4,649,042 | A | | 3/1987 | Davis et al. |
| 4,824,677 | A | * | 4/1989 | Shah ..................... A61K 9/2072 |
| | | | | 424/467 |
| 5,256,440 | A | * | 10/1993 | Appel et al. ................. 427/2.16 |
| 5,720,972 | A | * | 2/1998 | Munday ........................ 424/438 |
| 2009/0202634 | A1 | * | 8/2009 | Jans ..................... A61K 9/2018 |
| | | | | 424/468 |

FOREIGN PATENT DOCUMENTS

| EP | 0025699 | | 3/1981 |
|---|---|---|---|
| GB | 2306325 | A | 5/1997 |
| GB | 2326825 | | 1/1999 |
| WO | WO 8804923 | A * | 7/1988 |
| WO | WO-95/19763 | A1 | 7/1995 |
| WO | WO-02/089763 | A1 | 11/2002 |
| WO | WO 2005051487 | | 6/2005 |

OTHER PUBLICATIONS

Extended European Search Report in corresponding EP 13190620.8, Jun. 5, 2014.

* cited by examiner

*Primary Examiner* — Bethany Barham
*Assistant Examiner* — Lisbeth C Robinson
(74) *Attorney, Agent, or Firm* — Barnes & Thornburg LLP

(57) ABSTRACT

Disclosed is a bolus comprising: a bolus body comprising a matrix material and one or more biologically beneficial substances contained in and/or on the matrix; wherein the exterior surface of the bolus body is shaped so as to have a least one recessed portion; and at least part of the recessed portion of the bolus body is coated with a material which retards or inhibits release of the beneficial substance(s) from the matrix.

7 Claims, 4 Drawing Sheets

RECESSED BOLUS

FIELD OF THE INVENTION

The present invention relates to a bolus for administration to a ruminant animal and to a method of making the bolus.

BACKGROUND OF THE INVENTION

Ruminant animals, particularly when grazing or forage fed, may require prolonged administration of certain substances, beneficial nutritionally and/or medicinally, such as micronutrients (e.g. copper, selenium) or anthelmintics. Due to the difficulty and inconvenience of feeding substances and administering beneficial substances to grazing or forage fed animals, and to the desirability of individual animals receiving the correct amount of such substances, the practice is commonly employed of giving substances in a physical form, such as ruminal pellets known as boluses, which are retained in the ruminant fore-stomachs for prolonged periods, releasing beneficial substances.

Such substances may be released from the bolus by solution into the partly aqueous contents of the rumen (known as leaching, where the bolus matrix is itself insoluble) by gradual solution of the whole bolus (i.e. the bolus matrix is itself water soluble), or by erosion of the bolus.

It is typical of such boluses that the initial rate of release of the beneficial substance(s) is high, and later rates of release are reduced.

FIG. 1 shows mean plasma inorganic iodine levels in iodine-deficient cattle following administration of one or two wax-coated, leaching convex-surfaced iodine-releasing boluses, compared to untreated control animals. An initial sharp peak in the mean level in treated animals was followed by decline throughout the remaining period of release.

A typical target period of release for such boluses is six months. An ideal pattern of release would be entirely even, supplying a consistent and uniform release of beneficial substances throughout the life of the bolus.

It is known to form a bolus for administration to a ruminant animal using a mixture of three components: one or more beneficial substances to be released from the bolus (such as a mineral supplement or a therapeutic anti-parasitic agent), a ballast material (such as zinc, which increases the density of the bolus and helps to retain the bolus in the rumen), and a binder, such as a resin. It is further known to coat such a bolus with a protective coating of a substance with no, or very low, solubility in water (such as a wax), as described in GB 2,369,298. The protective coating prevents formation during storage of unsightly particles of the oxidised ballast metal, e.g. zinc oxide or iron oxide, and reduces the rate of leaching of water-soluble beneficial substance(s) from the bolus body. The protective coating is gradually abraded or eroded from the surface of the bolus body during the first week in the rumen.

In a variant of the sort of bolus described above, the use of coatings of different thicknesses over different parts of the bolus, and the use of a coating made from different substances at different parts of the bolus, is taught in GB 2,353,707. Both of these procedures increase complexity and cost in manufacturing. The concept of a bolus which may be only partially covered with a protective coating is disclosed in GB 2,333,451. GB 2,376,630 teaches a segmented bolus, which is intended to provide an intermittent, pulsed release of a beneficial substance, rather than a uniform, continuous rate of release.

It is an object of the present invention to provide a bolus which has more consistent and uniform rate of release of a beneficial substance than is obtainable with a conventional bolus.

SUMMARY OF THE INVENTION

In a first aspect the invention provides a bolus comprising: a bolus body comprising a matrix material and one or more biologically beneficial substances contained in and/or on the matrix; wherein the exterior surface of the bolus body is shaped so as to have at least one recessed portion; and at least part (typically all) of the recessed portion of the bolus body is coated with a material which retards or inhibits release of the beneficial substance(s) from the matrix. For simplicity of manufacturing, the thickness of the coating applied would normally be uniform over the whole surface of the bolus, and this is preferred but is not essential.

The bolus of the present invention is intended for administration to a ruminant animal and is adapted and configured to be retained in the animal's reticulo-rumen for an extended period of at least 2 months, more typically at least 4 months, preferably at least 5 months, more preferably at least 6 months and most preferably up to 12 months. The size and weight of the bolus can readily be adjusted to meet these criteria. The size of the bolus will also depend on the animal for which it is intended (e.g. goat, sheep or cow).

The matrix material may be any suitable material and may conveniently be a substance which has no, or very low, solubility in water (and is thus substantially insoluble in the reticulo-rumen). A preferred matrix material comprises a resin or a rosin, especially a pine rosin. Alternatively ethyl vinyl acetate, a wax or a mixture of the two may be employed, as also water-permeable concrete, finely porous porcelain or other ceramic material.

The biologically beneficial substance may be any one or more nutrients such as the trace elements selenium, cobalt, iodine, manganese, zinc and/or copper. Copper, selenium, iodine and cobalt are particularly beneficial nutrients for cattle and sheep. Zinc compounds such as zinc oxide or sulphate may be incorporated for nutritional supplementation or for control of fungal conditions such as facial eczema. Other beneficial nutrients which may be incorporated, possibly in conjunction with trace elements, are vitamins, lipids such as phospho-lipid, glycolipid or neutral lipid, and amino-acids. Alternatively, however, the biologically beneficial substance may be a medicament such as an anthelmintic, antibacterial substances, growth promoters, hormones, coccidiostats and/or flukicides, again either alone or in combination with nutrients.

The bolus body will preferably further comprise a ballast material, to increase the weight and density of the bolus. This is necessary to ensure the bolus is retained in the reticulo-rumen without being regurgitated or progressed into the subsequent chambers of the ruminant animal's stomach. Alternatively, regurgitation may also be prevented by known means such as wings or toggles, which obstruct escape of the bolus into the oesophagus or omasum.

The ballast material may be constituted by one or more of iron, manganese, copper, zinc or one or more compounds thereof, but is preferably constituted by elemental zinc. Results indicate that zinc and other ballasts are not appreciably lost during the life of the bolus.

The material used to coat at least the recessed portion of the bolus body is preferably a material with little or no solubility in water. Conveniently such coating material should be solid but preferably pliable or soft to the touch at 38-39° C. (the temperature to which the bolus will normally be exposed in the ruminant animal), such that the coating can be eroded or abraded in the reticulo-rumen. Suitable materials include, but are not limited to, paraffin wax, carnauba wax, beeswax, shellac, candelilla wax, and poly ethyl vinyl acetate. Most conveniently, the whole bolus is dipped or sprayed to give a uniform coating whose erosion is delayed on the recessed part or parts of the bolus.

If desired, the same (or a different) coating material may be applied to most or all of the exterior surface of the bolus body. Application of the same coating of the same or similar thickness to all (or substantially all) of the exterior surface of the bolus body facilitates manufacture. Methods by which the coating material may be applied to the bolus body include, for example, dipping in molten or dissolved preparations of coating material, spraying, and application by means of a coating pan.

The recessed portion of the bolus is such that abrasion or erosion of the protective or retardant coating from the recessed portion is inhibited or delayed. The recessed portion may be of any desired shape, but the applicant has found that one or more grooves or depressions, preferably along the long axis of the bolus body, are both convenient and effective. The width, length, and depth of the groove or depression (and the number thereof, if a plurality of grooves or depressions are employed), can be varied to determine the optimum phasing of release from different parts of the bolus. A preferred embodiment of the invention has a generally cylindrical bolus with one or more grooves or depressions on the surface thereof, which may be aligned along the long axis (or, less preferably, transversely across the bolus).

For example, narrow and/or deep grooves will be better protected from abrasion/erosion etc. in the reticulo-rumen than a wide and/or shallow groove. Thus, for instance, it may be desirable to provide one or more relatively wide and/or shallow grooves which will allow for relatively rapid uncoating and hence relatively rapid release of a beneficial substance, and to provide, on the same bolus, one or more relatively narrow and/or deep grooves which will cause greater delay uncoating of the bolus and hence permit release of the beneficial substance for a more prolonged period. In this way the different grooves will co-operate to provide sustained, relatively even release of the beneficial substance over a prolonged period. In another embodiment, a similar effect can be obtained by providing one groove which has different dimensions (in terms of width and/or depth) at different locations along its length. For example, a single groove may be provided in tapered form, being relatively wide and/or shallow at one end, and gradually narrowing and/or deepening along its length. Alternatively, instead of smooth tapering, the groove may alter in width and/or depth as step changes at different locations. Generally speaking it will be easier, and therefore generally preferable, to manufacture a bolus with a plurality of different-dimensioned grooves than to provide a bolus with a single groove of varying dimensions.

Desirably, the total area of the recessed portion of the bolus occupies between 10 and 75% of the surface area of the bolus body, preferably between 20 and 70%, more preferably between 30 and 65% and most preferably between 40 and 60%.

The term "recessed portion" preferably does not extend for present purposes, to boluses having a cavity or aperture passing through the full width or length of the bolus.

Where a plurality of recessed portions are formed on the bolus body, the recessed portions may be of the same dimensions and shape, or may be different. If a plurality of recessed portions are provided on the bolus body, they may be uniformly distributed over the surface of the body, or may be more numerous or more concentrated at one or more parts thereof (e.g. concentrated at one end region, or on one side, of the bolus). In one particular embodiment, a plurality (of about 4, 5 or 6) recessed longitudinal grooves are formed on the surface of the bolus body and substantially evenly distributed around the perimeter of an otherwise substantially cylindrical bolus body.

Recessed areas may be of various depths, widths and shapes, to give progressive increase in exposed surface area, as recessed portions of different configurations, which are hence protected to different degrees from abrasion, become exposed. In one preferred embodiment, the bolus body is substantially cylindrical with a generally circular section, but is formed with a longitudinal groove formed along one side and extending for most of the length of the bolus body (e.g. 50-99% of the length thereof), or formed with two longitudinal grooves, formed on opposed sides of the bolus body. Where two grooves are provided, the length thereof may be reduced but will preferably still extend over at least 50% of the length of the bolus body. The composition of the bolus body and of the coating applied thereto can be largely conventional: it is the shape and configuration of the bolus body which differs from conventional bolus designs, and which confers the advantages of the invention. The protuberant, or non-recessed, parts of the bolus are exposed by abrasion, permitting release of the beneficial substances to commence, whilst the recessed part or parts of the bolus remain protected by wax or other retardant coating, preventing early release of beneficial substance or substances from those parts. Release of beneficial substances from the more exposed parts of the bolus, whether by solution or erosion, commences after loss of any protective coating, just as it would from a waxed, smooth-surfaced cylindrical bolus of established type, within 7-10 days. Where the coated surface is partially protected from abrasion by being recessed, according to the invention, the coating persists, thus limiting the surface area of the bolus which is available for release of beneficial substances. Delayed exposure of the protected areas of the protected surface reduces early high levels of release, and gives an enhanced surface area for release when the entire surface becomes exposed, thus contributing to higher levels of release during the later life of the bolus, when declining release levels may otherwise result in reduced effectiveness of the bolus.

It has been demonstrated that some elements, in particular salts of selenium and iodine, release from a leaching bolus most readily when present in the same bolus. Cobalt salts release most readily in the absence of the other commonly supplemented elements. Employment of different shapes of non-recessed and recessed areas allows shapes which permit two different boluses to be administrated side by side rather than end to end, thus reducing the risk of throat damage caused by an excessively long dosage form.

In one particular embodiment, the invention provides a co-operating pair of boluses, each being in accordance with the first aspect of the invention as aforesaid, the pair of boluses being shaped and dimensioned so as to fit, simultaneously, in a "side-by-side" arrangement, within a conventional prior art dosing gun used to administer boluses to cattle. In one such embodiment one of the pair of boluses comprises a salt of selenium and/or iodine and the other of the pair of boluses comprises a salt of cobalt.

The Applicant has also discovered another advantage in a bolus according to the invention. In a conventional, substantially cylindrical, bolus body, beneficial substances contained within or near the centre of mass of the bolus are, relatively speaking, a long way from the surface of the bolus body and therefore are slow to leach out. Since the bolus may expand after several months in the rumen, its density may be reduced and it may be regurgitated, or advanced from the reticulo-rumen, before the entire dose of beneficial substances has leached from the bolus, which is inefficient and wasteful. In contrast, in a bolus according to the invention, the recessed portion, once exposed by removal of the protective coating, leads to the central part of the bolus being closer to the aqueous environment of the reticulo-rumen, thereby facilitating leaching of the substances from the central part of the bolus. As a result, it is more likely that more of the beneficial substance(s) from the central part of the bolus will be released before the bolus is regurgitated or advanced from the reticulo-rumen, so that the animal receives more of the beneficial substance(s) originally contained within the bolus.

In a second aspect, the invention provides a method of making the bolus of the first aspect, the method comprising the steps of: forming a bolus body comprising a matrix and one or more biologically beneficial substances contained in the matrix, or which may constitute the matrix, the bolus body having at least one recessed portion; and coating at least part of the recessed portion of the bolus body with a material which retards or inhibits release of the beneficial substance(s) from the matrix.

Generally, the method of the second aspect will be such that performance of the method will result in production of a bolus having one or more of the preferred features recited above in relation to the first aspect of the invention.

Bolus bodies for a bolus in accordance with the first aspect of the invention may be formed by for example moulding, extrusion or compression. Coatings to delay onset of release may cover part or all of the bolus. They should preferably be of little or no aqueous solubility at a temperature of 38-39° C., and should desirably be solid or pliable or soft to touch at 38-39° C. Suitable materials include, but are not confined to, paraffin wax, carnauba wax, beeswax, shellac, candelilla wax and poly ethyl vinyl acetate.

Methods by which the coating may be applied to the bolus include, but are not confined to, dipping in molten or dissolved coating material, spraying, powder coating, and application by means of a coating pan.

The intervention will now be further described by the way of illustrative examples and with reference to the accompanying drawings, in which:

FIG. 2 (b) is a plan view of the same conventional bolus;

Figure 3:
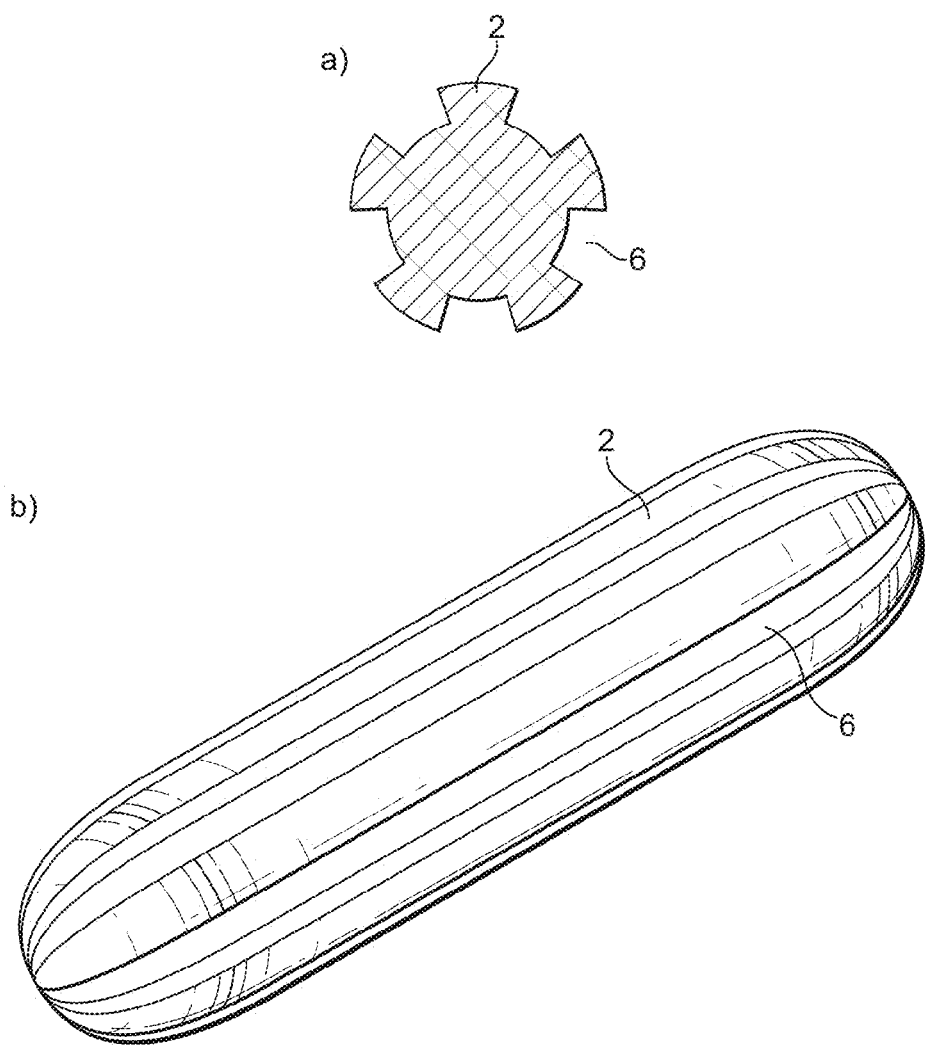
Figure 4:
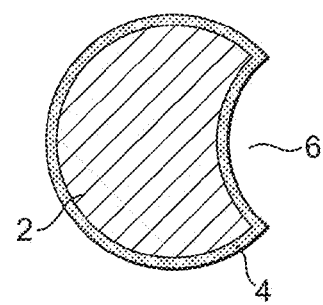
Figure 5:
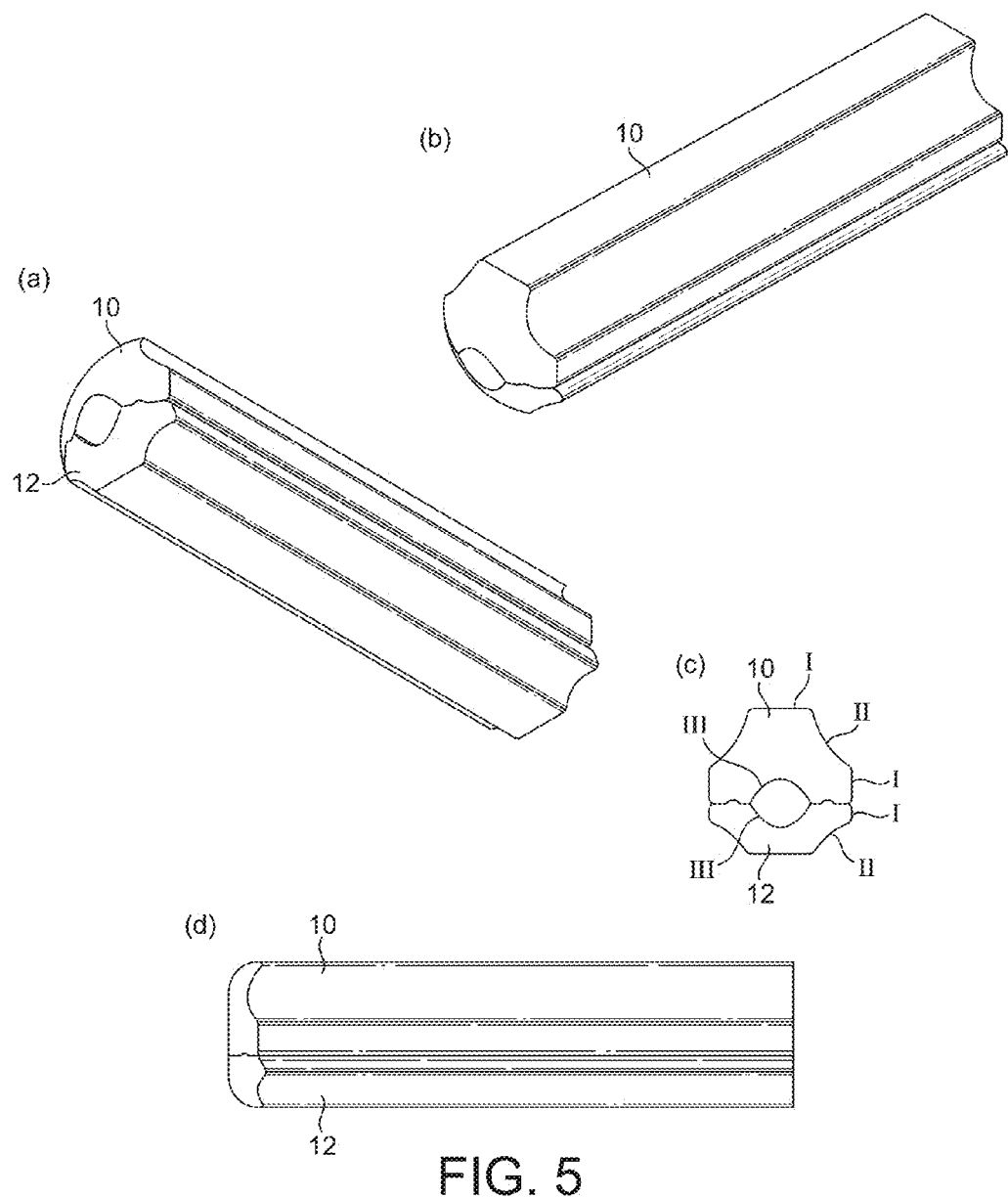

FIGS. 3 (a) and 3 (b) show, respectively, a transverse section and a plan view of one embodiment of a bolus body (prior to coating with a release inhibitor) for use in a bolus in accordance with the invention;

FIG. 4 is a transverse sectional view of a different embodiment of a coated bolus in accordance with the invention; and FIG. 5 (a)-(d) show various views of two different embodiments of a bolus in accordance with the invention which, in the illustrated embodiment, are administered in a laterally paired (side-by-side) relationship, optionally defining a cavity between the two boluses.

EXAMPLES

Figure 1:
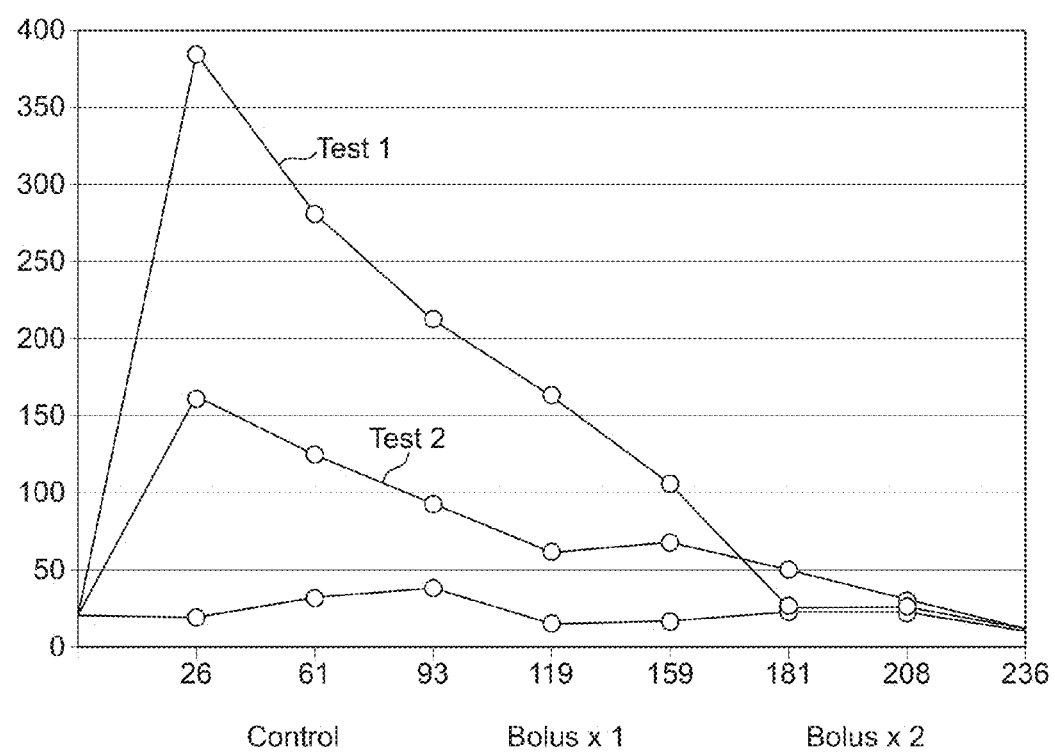
FIG. 1 is a graph of mean plasma inorganic iodine levels (in μg/liter) in iodine-deficient cattle following administration of either one (Test 2) or two (Test 1) conventional leaching (convex surfaced) iodine-releasing boluses, against time (days), compared to levels in untreated control animals.

FIG. 1 is a graph illustrating mean levels (μg/liter) of inorganic iodine in plasma from iodine-deficient cattle having received one (Test 2) or two (Test 1) conventional convex-surfaced iodine releasing boluses (of the sort illustrated in FIG. 2), against time (in days), compared with control animals which did not receive any bolus. As can be seen from the graph, the level of iodine in the control animals remains low throughout the period of the trial. In both of the test groups, there was an initial sharp rise in level of iodine (peaking at around day 26), followed by a steady decline throughout the rest of the trial period, returning to the levels seen in the control animals by about days 181-208. The present invention aims to provide a bolus which provides for more consistent even release of a beneficial substance over a sustained period.

Example 1

Comparative Example

Figure 2:
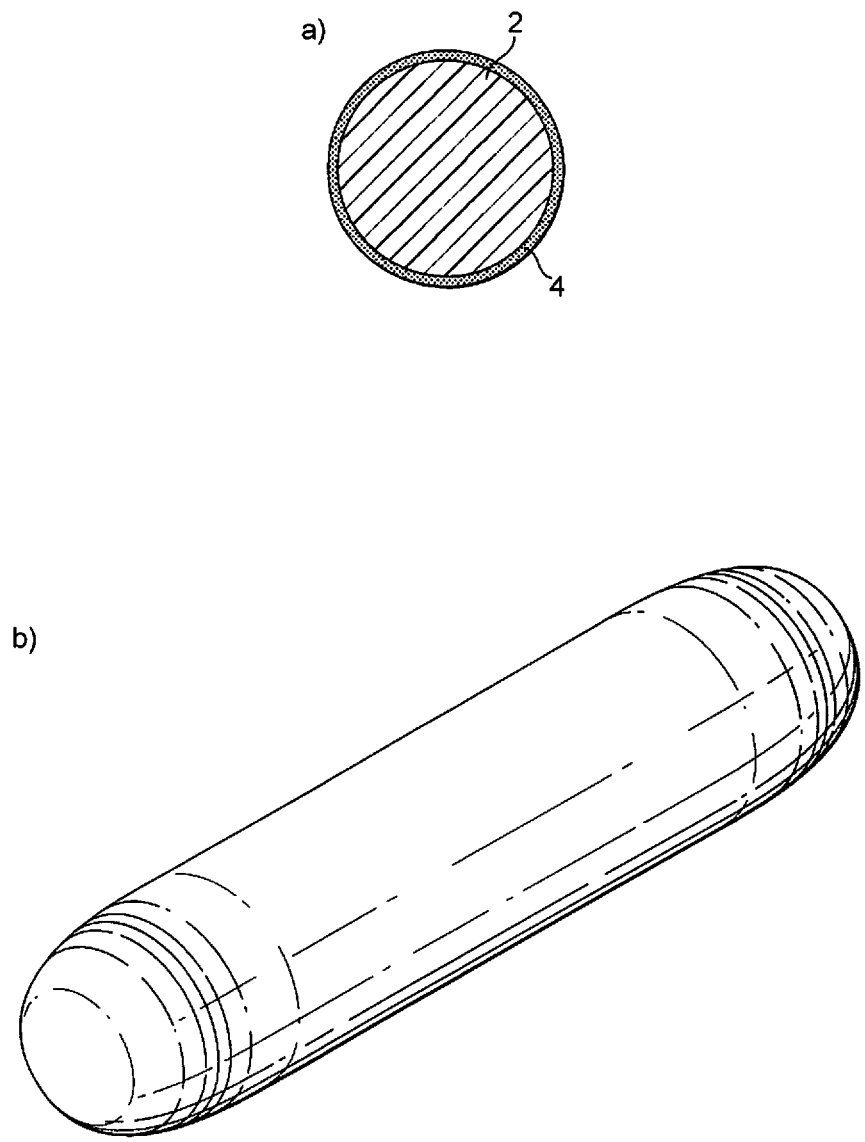
FIG. 2 (a) is a transverse sectional view through one embodiment of a conventional bolus.

A smooth cylindrical bolus was prepared as illustrated in FIG. 2, of length 55 mm, diameter 20 mm, weight 58 g and having the following composition:—

| | |
|---|---|
| Resin binder: | 16.24 g |
| Metallic zinc particles 45-55 microns, (densifier): | 72.09 g |
| Calcium iodate: | 9.65 g |
| Sodium selenite: | 2.02 g |
| | 100.00 g |

The materials were mixed, melted with agitation at 140° C. for 20 minutes, and moulded in a smooth, cylindrical rubber mould. The bolus was coated by dipping in beeswax at 100° C., forming a coating with a thickness of approx. 1 mm. Referring to FIG. 2 (a) the bolus body (2) is shown with the beeswax coating (4).

The bolus was placed in the reticulum of a rumen fistulated bullock, and removed for examination after 7 and 14 days. Loss of coating from the surface of the bolus was estimated by visual inspection as follows:—
loss after 7 days: 95%; and loss after 14 days: 100%

Example 2

Four boluses A1, A2, B1, B2 were prepared, having the same composition as Examples 1, 3 and 4 and having the following overall dimensions: length 49 mm diameter 25 mm weight 58 g. All the bolus bodies had five equally spaced longitudinal grooves, each of 7 mm width at the surface, and of 5 mm depth, with flat sides radially aligned. The total surface area of each bolus was 6458 mm$^2$, and the total recessed surface area was 2553 mm$^2$. The bolus bodies were thus substantially as shown in FIGS. 3 (a) and (b).

FIGS. 3 (a) and 3 (b) show the bolus body (2) prior to coating. The bolus body has five longitudinal grooves, a representative one of which is indicated by reference numeral (6).

Melted beeswax was applied to the grooves only of bolus B1 and B2, to a depth of 1 mm—the rest of the (B) boluses were uncoated, and no coating at all was applied to the (A) boluses.

Release of iodine from the four boluses was compared in vitro, as follows. Each bolus was placed in 200 ml of distilled water in a 250 ml conical flask. All four flasks were placed in an incubated orbital shaker having a 20 mm movement radius at a temperature of 37° C. The shaker was set running at 160 rpm, to represent the abrasive action of a rumen. Following 3, 7, 11 and 13 days treatment, the liquids in the flask were removed for iodine analysis, and replaced by 200 ml fresh distilled water. Analysis of iodine by titration revealed the loss from each bolus per day to be as shown in Table 1.

TABLE 1

Mean iodine release per day from recessed boluses, either uncoated (A) or coated in recessed grooves (B).

| Iodine Released Per Day | Mean A (mg) | Mean B (mg) |
| --- | --- | --- |
| Days 0-3 | 28.16 | 14.43 |
| Days 3-7 | 10.30 | 2.91 |
| Days 7-11 | 4.75 | 1.58 |
| Days 11-13 | 3.96 | 1.06 |
| Total release, Days 0-13 | 152.6 | 63.37 |

Conclusion:

The release over a 13 day period from uncoated recessed boluses exceeded that from identical boluses where the recessed areas were protected from exposure to aqueous medium by coating by a factor of about 2.4:1.

The surface area of the uncoated boluses (6458 $mm^2$) exceeded the uncoated areas of the recessed boluses (2553 $mm^2$) by a factor of 2.5:1.

The result shows that protection of a proportion of the surface area of a leaching ruminal bolus by an impervious coating, such as wax, reduces the rate of release of dissolved beneficial substance from the bolus by a proportion similar to the reduction in exposed surface area from which leaching can occur.

If one compares the total mean iodine release from uncoated boluses A, over days 0-13, with that from boluses B, it is apparent that the uncoated boluses released 2.4 times more iodine than the uncoated boluses. Thus, a bolus in accordance with the invention releases a beneficial substance more slowly, and over a more prolonged period. In contrast, a grooved, but uncoated bolus, releases a beneficial substance very rapidly initially. This initial "spike" of release is greatly reduced by using a bolus in accordance with the invention.

Example 3

A bolus of the same composition and weight as in Example 1 was prepared in the same way, but was moulded in a rubber mould shaped to form a 25 mm diameter bolus, with longitudinal channels on the surface of the mould. Bolus length was 49 mm. The bolus body was thus substantially as shown in FIGS. 3 (a) and (b). 45% of the peripheral surface is taken up with channels, 7 mm wide at the surface and 5 mm deep with flat sides radially aligned. The bolus was coated with beeswax to a thickness of 1 mm as for Example 1.

The bolus was placed in the reticulum of a rumen-fistulated bullock, and removed for examination after 9, 20, 48, 59 and 70 days.

Loss of coating from the non-recessed parts of the bolus was estimated as follows:
Loss after 9 days: 100%
Loss of coating from the recessed parts of the bolus (i.e. parts partially protected from abrasion within the rumen)
Loss after 9 days: 5%
Loss after 20 days: 10%
Loss after 48 days: 20%
Loss after 59 days: 50%
Loss after 70 days: 80%
Repetition of this procedure with 5 similarly prepared boluses gave similar results.

Conclusion:

If parts of the surface of a ruminal bolus coated with a protective material, such as wax, are recessed, thus to reduce abrasion caused to that part of the surface by contact with the fibrous and abrasive contents of the rumen, the rate of loss of the coating is reduced. Coatings are removed more slowly from depressions, or concavities or otherwise recessed parts of the surface of boluses than from the convex surface.

Example 4

A bolus of the same composition and overall dimensions as in Example 1 was prepared by moulding, to have a single concave channel 14 mm wide at the surface and 7 mm deep with sides radially aligned. This is shown in transverse section in FIG. 4. Referring to FIG. 4, the bolus body (2) has a single shallow channel, denoted generally by reference numeral (6). The whole of the bolus body is coated with a thin layer of beeswax (4) as a release—inhibiting coating. The bolus was coated with beeswax in the same way as for Example 1 (FIG. 2).

This bolus was also placed in the reticulum of a rumen fistulated bullock and removed at intervals for examination.

Loss of coating from the intact circumference of the bolus was estimated as follows:
Loss after 7 days: 100%
Loss of coating from the channel (i.e. part of surface partially shielded from abrasion within the rumen).
Loss after 7 days: 20%
Loss after 11 days: 50%

This compares with a 5% loss of coating after 9 days and a 10% loss after 20 days, which was found with Example 3, where the grooves forming the recessed areas were narrower, giving more protection from abrasion to the recessed surface.

Conclusion:

Different configurations by which loss of surface coatings from boluses may be delayed are possible and may result in different rates of release of beneficial substances.

Example 5

FIG. 5 shows views of two boluses according to the invention with recessed areas of differing widths and depths on each bolus. FIGS. 5(a) and 5(b) are perspective views, FIG. 5(c) is an end elevation and FIG. 5(d) is a side elevation. The larger bolus, 10, contains salts of selenium and iodine in the formulation as for Example 1. The smaller bolus, 12, contains cobalt acetate, plus rosin powder and zinc densifier as for Example 1. Both are coated with 1 mm of beeswax. They may be given together laterally aligned, side-by-side, although once in the animal they will become separated. The cavity thus formed between the two boluses may contain a third bolus (or capsule) such as one containing copper oxide needles.

Note that the recessed areas of both boluses are of two different configurations. In both boluses, recessed area II is less protected from surface abrasion than recessed area III. As best seen in FIG. 5c, the radius of curvature of recessed surface III is smaller than that of slightly recessed surface II. This allows staged released from the different parts of each bolus, with the coating being lost progressively from the surface areas, as follows:—
I. Non-recessed surfaces
II. Slightly-recessed surfaces
III. Recessed surfaces

The invention claimed is:

1. A pair of co-operating boluses, each of the pair of boluses being generally hemi-cylindrically shaped so as to form a cylindrical bolus, said pair of co-operating boluses being dimensioned so as to fit, simultaneously, in a side-by-side arrangement, within a conventional oral dosing gun used to administer boluses orally to cattle, wherein each of the pair of co-operating boluses comprises a bolus body comprising a matrix material and one or more biologically beneficial substances mixed with the matrix; wherein the exterior surface of the bolus body is shaped so as to have either:
   at least a first groove having a first width and depth, and at least a second groove having a second width and depth, wherein the second width is less than the first width and/or the second depth is greater than the first depth; or
   at least one groove which differs, in terms of width and/or depth, at different locations along its length;
   said first and second grooves, or said variably dimensioned groove, being aligned along the long axis of the bolus;
   the bolus body, including said groove(s), being coated with a substantially uniform thickness of a coating material which retards or inhibits release of the beneficial substance from the matrix, such that the first and second grooves become uncoated at different rates, or the variably dimensioned groove uncoats at different rates at said different location, thereby achieving variable rates of release of the beneficial substance(s) from the matrix.

2. A pair of co-operating boluses according to claim 1, wherein the matrix material comprises one or more of: a resin, a rosin, poly ethyl vinyl acetate, a wax, a water-permeable concrete or finely porous porcelain.

3. A pair of co-operating boluses according to claim 1, wherein the body further comprises a ballast material.

4. A pair of co-operating boluses according to claim 3, wherein the ballast material comprises one or more of iron, manganese, copper, zinc or compounds comprising any thereof.

5. A pair of co-operating boluses according to claim 1, wherein the coating material used to coat at least the recessed portion of the bolus body comprises one or more of: paraffin wax, carnauba wax, beeswax, shellac, candelilla wax, and poly ethyl vinyl acetate.

6. A pair of co-operating boluses according to claim 1, wherein the coating material is applied over the whole surface of each co-operating bolus.

7. A method of making a pair of co-operating boluses in accordance with claim 1, the method of making each co-operating bolus of the pair of co-operating boluses comprising the steps of:
   (i) forming a hemi-cylindrically shaped bolus body comprising a matrix and one or more biologically beneficial substances contained in the matrix, or which may constitute the matrix, the bolus body having either:
   at least a first groove having a first width and depth, and at least a second groove having a second width and depth, wherein the second width is less than the first width and/or the second depth is greater than the first depth; or
   at least one groove which differs, in terms of its width and/or depth, at different locations along its length;
   said first and second grooves, or said variably dimensioned groove, being aligned along the long axis of the bolus;
   (ii) coating at least part of the groove(s) with a material which retards or inhibits release of the beneficial substance(s) from the matrix, such that the first and second grooves become uncoated at different rates, or the variably dimensioned groove uncoats at different rates at said different locations, thereby achieving variable rates of release of the beneficial substance(s) from the matrix.

* * * * *